United States Patent [19]

Vegega et al.

[11] Patent Number: 5,393,781
[45] Date of Patent: Feb. 28, 1995

[54] METHOD FOR CONTROLLING ZEBRA MUSSELS

[75] Inventors: Alexander M. Vegega, Trenton, N.J.; Claudio E. Manissero, Lincoln University, Pa.

[73] Assignees: FMC Corporation, Philadelphia, Pa.; The Research Foundation of the State University of New York, Albany, N.Y.

[21] Appl. No.: 88,935

[22] Filed: Jul. 8, 1993

[51] Int. Cl.$^6$ .............................................. A01N 37/16
[52] U.S. Cl. .................................. 514/557; 424/613; 424/616
[58] Field of Search .................... 514/557; 424/613

[56] References Cited

U.S. PATENT DOCUMENTS

| | | | |
|---|---|---|---|
| 3,122,417 | 2/1964 | Blaser et al. | 23/207.5 |
| 4,324,784 | 4/1982 | Naito et al. | 424/130 |
| 4,997,574 | 3/1991 | Sarunac | 210/739 |
| 5,015,395 | 5/1991 | Muia et al. | 210/755 |
| 5,040,487 | 8/1991 | Bollyky et al. | 119/4 |
| 5,160,047 | 11/1992 | McCarthy | 210/749 |
| 5,192,451 | 3/1993 | Gill | 210/755 |
| 5,209,934 | 5/1993 | Ekis, Jr. et al. | 424/661 |
| 5,240,674 | 8/1993 | Armor | 422/6 |
| 5,256,310 | 10/1993 | Brooks | 210/747 |

FOREIGN PATENT DOCUMENTS 58-23608 2/1983 Japan.
59-212414 12/1984 Japan.

OTHER PUBLICATIONS

Chin, Choo D., "Neutralization of Shellfish Poison by Chemical Disnfectants", Apr 28, 1969, Toxicology and Applied Pharmacology 16, pp. 430–433 (1970).

*Primary Examiner*—Peter O'Sullivan
*Assistant Examiner*—B. Burn
*Attorney, Agent, or Firm*—Patrick C. Baker; Anthony L. Cupoli

[57] ABSTRACT

Method of controlling the zebra mussel by direct contact with peracetic acid or indirectly by application to an environment where control is desired. The biofouling of environments, such as fresh water intakes, conduits and storage systems of power and water treatment systems, and of processing streams of industrial plants, is thereby reduced or eliminated.

10 Claims, No Drawings

METHOD FOR CONTROLLING ZEBRA MUSSELS

BACKGROUND OF THE INVENTION

This invention relates to a method for controlling the zebra mussel. The invention more particularly concerns the eradication of the zebra mussel in aqueous environments including water intakes, conduits and storage systems of power and water treatment plants, and processing streams and systems of industrial plants.

The zebra mussel (Dreissena polymorpha), endemic to the Black and Caspian Seas, is unique among mollusks because it thrives only in fresh water bodies; reproduces at an astonishing rate (research suggests the female can produce more than 1 million eggs yearly); is inedible by humans; has a microscopic larval stage (veliger) that is carried, often undetected, by water currents and human activities to a multitude of environments; can survive out of water for extended periods (estimated as up to 14 days); has a relatively long life span (about five years); has sticky, hair-like threads (byssuses) which enable the mussels (both veligers and adults) to attach tenaciously to virtually any hard surface; and has a voracious appetite for microscopic plants and animals.

Since its discovery in June 1988 in Lake St. Clair, Mich., the zebra mussel has spread to all of the Great Lakes and to many inland rivers of the eastern and midwestern United States, including the Mississippi, Hudson, Ohio and Susquehanna rivers. The mussel has caused an estimated $100 million in damage to date in the United States and Canada. The damage is to inlet water systems of power and water treatment plants, to water filtration systems and conduits of industrial plants, and to boats and marine engines and pumps, caused by incrustation of the mussels on inlet and conduit surfaces. The biofouling results in severe restriction and even interruption of flow, thus affecting municipal and power plant water supplies, and industrial processes dependent on water intake from fresh water bodies.

The mussels have seriously affected the ecological balance in fresh water bodies by destroying crayfish and other humanly edible shellfish, by creating barriers in the spawning grounds of game fish, and by filtering out microscopic plants and animals that serve as food for other marine life.

It is estimated that zebra mussels concentrate contaminants about 100 times more than do fish. Thus, predators of the mussels, such as diving ducks and certain fish, can be expected to be exposed to high contaminant concentrations.

These and other threats to water use posed by zebra mussel infestations have motivated a variety of approaches to control. In addition to mechanical removal of incrustations on a periodic basis and redesign of water inlets to reduce ideal conditions for infestation, thermal backflushing and chemicals have been used. In thermal backflushing, heated discharge water in a power plant is re-directed to cool water intakes to kill the zebra mussels. The treatment has the disadvantage of sometimes resulting in fish kills.

The chemical treatments reported to date have been non-selective, too toxic for use in many waterways, too corrosive, or lacking in reasonable handling safety and/or cost. For example, although effective, chlorine treatment is accompanied by formation of toxic by-products such as trihalomethanes and therefore cannot be used where there may be human exposure. When halides are used, it is often necessary to de-toxify streams before end use, thus adding significantly to treatment cost.

Other oxidants, such as ozone and/or hydrogen peroxide, are environmentally safe but pose safety and handling problems (ozone) or are not sufficiently active to be cost effective (hydrogen peroxide).

SUMMARY OF THE INVENTION

It has been discovered that peracetic acid effectively controls the zebra mussel at reasonable cost and with no harmful impact on water quality. Moreover, peracetic acid can be handled, delivered to treatment sites, and introduced to environments where control is desired, with relative ease and safety.

DETAILED DESCRIPTION

Peracetic acid, also known as peroxyacetic acid, is a commercial product sold under various brand names including the VigorOx trademark of FMC Corporation. The VigorOx product is registered with the U.S. Environmental Protection Agency as a liquid sanitizer. Commercial products are equilibrium mixtures, in aqueous solution, of peracetic acid, acetic acid and hydrogen peroxide, and optionally, but usually, contain a stabilizer for the peracetic acid. A variety of stabilizers are useful and include the phosphates, phosphonic acids and dipicolinic acids described in U.S. Pat. Nos. 2,590,856, 2,609,391, 3,122,417, 4,051,058, 4,297,298, PCT Patent Publication WO 91/07375, and in other literature. Preferred stabilizers are the phosphonic acids of U.S. Pat. No. 3,122,417. The stabilizers may be added in any desirable amounts, for example about 0.1–10 wt % on total formulation, preferably about 0.5–3 wt % on the same basis.

Commercial peracetic acid is available in concentrations ranging from about 1 wt % to about 40 wt %. Depending on the circumstances, almost any form or concentration of peracetic acid can be used for control of the zebra mussel in accordance with the invention. However, it is preferred in most applications for reasons of safety to use dilute aqueous formulations, containing about 1–10 wt % peracetic acid, the balance being the appropriate equilibrium concentrations of acetic acid, hydrogen peroxide and water, with stabilizer being present as an additive.

Treatment can be by direct contact with the mussel, either as veligers or adults, but more usually the treatment will be by addition of suitable doses of peracetic acid at the point of water intake or by addition to water conduits or water storage areas of power plants, water treatment facilities and industrial plants affected by the mussel.

It has been observed that control of the adult mussel in aqueous environments characterized by continuous flow of water, as would be the case at inlets to power plants, begins to be effective at peracetic acid concentrations of about 0.1 ppm (100% basis), as supplied, for example, by 2 ppm of a peracetic acid solution containing 5 wt % peracetic acid.

Greater control of the adult mussel in such environments is obtained at higher concentrations, of the order of 0.2 ppm (100% basis) or higher. A preferred peracetic acid concentration for moving water environments is 0.5 ppm (100% basis) or more.

Dosing with the peracetic acid may be singly, intermittent or continuous, or may be on a maintenance basis, and may be varied or adjusted, along with concentration, depending on mussel density, water flow and temperature, physical circumstances, and other parameters of the treatment site. For example, in quiescent environments such as ponds, reservoirs or holding tanks, single treatments upon observation of mussels may be sufficient. In other cases, where flow is continuous, it may be necessary to inject on schedule, either intermittently or continuously, using known regulated injection mechanisms.

The peracetic acid may be delivered to the treatment site in any convenient manner. It may be drummed or tanked to the site, or delivered from bulk storage by piping or other suitable conduits, and applied to the environment requiring treatment, using any of the conventional chemical delivery systems, including pumps, valves, flow regulators, eductors, diffusers, contact chambers, and the like. The reagent may also be generated on site from reactors.

Other reagents may be used in combination with the peracetic acid. These reagents may be other biocides, including molluscicides, both oxidizing and non-oxidizing, or may be additives for enhancement of the activity of the peracetic acid or for other functions in support of the biocidal activity of peracetic acid. Oxidizing reagents include ozone, potassium permanganate, hydrogen peroxide, and various hydrogen peroxide generators such as persulfates (alkali metal, ammonium); perborates; and organic compounds such as urea/hydrogen peroxide adducts. Other oxidizing reagents include the halogens, halogen generating compounds, and halides, such as hypochlorites, hypochlorous acid, monochloroamine and chlorine dioxide, and combinations of halogens such as the "Acti-Brom" bromine/chlorine product sold by Nalco Corporation. Typically, the peracetic acid treatment may be combined with chlorination, as described in U.S. Pat. No. 4,997,574.

Non-oxidizing biocides include various potassium compounds such as $KH_2PO_4$ and KCl, quaternary ammonium compounds such as poly(oxyethylene(dimethyliimino)ethylene(dimethylimino)ethylene dichloride), antifouling paints based on copper, phosphates, tributyl tin and other metals or metal compounds, and plant extracts such as lemmatoxin.

In some cases it may be useful to combine surfactants with peracetic acid treatment to assist in dispersion of the peracetic acid or other biocides used in combination with peracetic acid, or to add antifoaming agents if foaming is a hindrance to contact of the peracetic acid with the zebra mussels. Suitable surfactants include anionics, cationics or nonionics, of which the anionic sulfates and sulfonates are representative, as described in U.S. Pat. Nos. 4,051,058 and 4,051,059.

The following example is intended as further illustration of the invention but not to limit the scope thereof. All parts and percentages in the example, and throughout this specification and claims, are by weight and all temperatures are centigrade, unless otherwise indicated.

EXAMPLE

Test Products

Three oxidants were tested and compared for zebra mussel control:
Product A: chlorine as a sodium hypochlorite (NaClO) stock solution containing the NaClO at a nominal concentration of 1 g/L (0.1 wt. %).

Product B: potassium persulfate ($K_2S_2O_8$) as a stock solution at a nominal concentration of 5 g/L (0.5 wt. %).

Product C (invention): peracetic acid ($CH_3CO_3H$) as a stock solution at a nominal concentration of 50 g/L (5 wt. %) having the following composition:

|  | Wt. % |
| --- | --- |
| peracetic acid | 5.1 |
| hydrogen peroxide | 21.7 |
| acetic acid | 10.4 |
| stabilizer* | 0.7 |
| water | 62.1 |
|  | 100.00 |

*1-hydroxyethylidene-1,1-diphosphonic acid

Test Procedure

The oxidant products were tested in a continuous flow system. Water from the Niagara River was allowed to fill a constant head tank. The water flowed by gravity from the constant head tank to each of six continuous flow stirred tank reactors (CFSTRs). Prior to the tests, adult zebra mussels were collected from Tonawanda Creek and the Niagara River and stored in aquaria receiving Niagara River water continuously to acclimate the mussels to the water. Live mussels of a uniform size were selected for the tests. Mussels were placed in plastic mesh baskets which were suspended into each CFSTR. Ten mussels were placed in each of the 10 subsections of the baskets, resulting in 100 mussels for each test. Oxidants were dosed into the CFSTRs by pumping from the stock solutions using peristaltic pumps through tees located upstream of the CFSTRs. Stock solution concentrations were one thousand times the nominal oxidant doses.

The tests were conducted in two phases. In the first phase, Products B and C were tested at two doses each. Based on the results of the first phase, a second phase was designed to examine Product C at two additional doses.

For each phase, six (Phase I) or four (Phase II) reactors were used simultaneously. In each phase, one reactor served as a control and received no oxidant. A second reactor received chlorine (Product A) at a nominal dose of 1 mg/L. The remaining reactors received Products B and C.

Residual chlorine from Product A was measured in the reactor effluent by the DPB colorimetric method. The concentrations of Products B and C were calculated from the stock solution concentrations and the measured flow rates of Niagara River water and oxidant. Niagara River water flow rates were determined with a graduated cylinder and stopwatch. All tests were conducted at the ambient river temperature. Temperature was measured by a mercury thermometer. In a typical run, temperature was measured daily and the Niagara River water flow rate was measured twice daily.

Mussel mortality was determined by withdrawing mussels from a randomly selected subsection of the mesh basket at desired intervals. Observations were made and recorded concerning mussel activity. The selected mussels were placed in aquaria receiving fresh Niagara River water continuously for a period of 48 hours. Previous work with chlorine (Product A) has indicated that a 48 hour recovery period is adequate for assessing mussel mortality. At the end of the 48 hour recovery period, the mussels were examined and scored as alive or dead. Mussels were scored as alive if they responded to gentle probing. All other mussels were scored dead.

Test Results

The experimental conditions for each run are shown in Table 1 where "PAA" indicates peracetic acid. The average water temperature in Phase I was 20.1° C. (standard deviation: 0.1° C.). The average water temperature in Phase II was 20.5° C. (standard deviation: 0.1° C.). In the test results, Product B and C concentrations are given on a total basis. Product B was 100% active, but Product C was only 5% active. Active concentrations for products are given in parentheses following the total concentrations in the tabulations of test results.

TABLE 1

Conditions for Each Mortality Study

| Phase | Oxidant | Avg. Oxidant Conc. ± Std. Dev. (mg/L) | Duration (hr) |
|---|---|---|---|
| I | No oxidant (control) | 0 | 177.25 |
| | Product A (chlorine) | free: 0.78 ± 0.17 total: 0.98 ± 0.18 | 177.25 |
| | Product B ($K_2S_2O_8$) | 5.0 ± 0.1  25 ± 1 | 177.25 177.25 |
| | Product C (PAA) | 2.1 ± 0.2 (0.11 ± 0.1) 22 ± 4 (1.1 ± 0.2) | 177.25 177.25 |
| II | No oxidant (control) | 0 | 217.75 |
| | Product A (chlorine) | free: 0.78 ± 0.12 total: 0.01 ± 0.10 | 103.75 103.75 |
| | Product C (PAA) | 4.8 ± 0.4 (0.24 ± 0.02) 10.2 ± 0.8 (0.51 ± 0.04) | 217.75 217.75 |

Mussel mortality data for all experimental runs are given in Tables A.1–A.10. Mortalities for the runs in Phase I are in Tables A.1 through A-6 and mortalities for runs in Phase II are in Tables A.7 through A.10.

Comparing the percent mussel mortalities with Product B in Phase I and with chlorine (Product A) and no oxidant, it is seen that low mortality resulted at nominal concentrations of Product B up to 25 mg/L. In contrast, chlorine (Product A) yielded 50% mortality after about 3–4 days and 100% mortality after about 7 days. The results with chlorine (Product A) are consistent with prior experiences at a comparable water temperature.

Comparing the percent mussel mortalities with Product C in Phase I and with chlorine (Product A) and no oxidant, it is seen that very little mortality was observed at a nominal concentrations of 2 mg/L (active concentration 0.1 mg/L) or in the no oxidant (control) reactors. In contrast, chlorine at 1 mg/L and Product C at 20 mg/L (1 mg/L active) were about equally effective. Both oxidants yielded 50% mortality after about 3–4 days and 100% mortality after about 6–7 days.

Based on the results on Phase I, it was decided to forgo further testing of Product B and focus on the effects of Product C concentration on mussel mortality. In Phase II, Product C concentrations of 5 and 10 mg/L (0.25 and 0.5 mg/L active) were examined and the percent mussel mortality with Product C compared to chlorine (Product A) and no oxidant.

The data shows that initially Product C at 5 and 10 mg/L (0.25 and 0.5 mg/L active) was not as effective as chlorine (Product A) at 1 mg/L for killing adult zebra mussels but that efficacy increased with treatment time. Thus, fifty percent mortality was achieved in about 5 and 8–9 days with Product C at 5 and 10 mg/L (0.25 and 0.5 mg/L active), respectively. Complete mortality was achieved in about 7 days with Product C at 10 mg/L (0.5 mg/L active) and after about 9 days at 5 mg/L (0.25 mg/L active). Again, little mortality was observed in the no oxidant controls.

Probit Analysis Comparison

The effect of Product C dose on mussel mortality was investigated by calculating the time to mortality of one-half the mussels ($T_{50}$) at each dose. The $T_{50}$ values were determined by probit analysis (see explanation below) and are listed in Table 2. The $r^2$ values in Table 2 are from linear regression of the probit plots and indicate the degree of fit in the probit plots ($r^2 = 1.0$ means the linear regression model fit the data exactly).

TABLE 2

Time to 50% Mortality for Products C and A

| Avg. Oxidant Conc. (mg/L) | $T_{50}$ (days) | $r^2$ |
|---|---|---|
| Product C: | | |
| 4.8 (0.24 active) | 9.3 | 0.859 |
| 10.2 (0.51 active) | 5.1 | 0.834 |
| 22 (1.1 active) | 3.4 | 0.944 |
| Product A: | | |
| 1.1 mg/L total chlorine | 3.9 | 0.951 |

As shown in Table 2, the $T_{50}$ values ranged from 3.4 days for a Product C concentration of 22 mg/L (1.1 mg/L active) to 9.3 days for a Product C concentration of 4.8 mg/L (0.24 mg/L active). A $T_{50}$ value could not be calculated for the Product C concentration of 2.1 mg/L (0.11 mg/L active) and all Product B and no oxidant (control) runs because so little mortality was observed.

The $T_{50}$ values permit comparison of the oxidants. For example, the time to 50% mortality ($T_{50}$) for Product C at 22 mg/L (1.1 mg/L active) was slightly less than chlorine (Product A) at 1 mg/L total chlorine (0.78 gm/L free chlorine). Thus, Product C at 22 mg/L (1.1 mg/L active) killed adult zebra mussels slightly faster than chlorine at 1 mg/L total chlorine.

Probit Analysis Explanation

Probit analysis is a standard technique for analyzing data which follow the cumulative normal distribution curve. Plots of zebra mussel mortality versus time are "S-shaped" and can be described by the cumulative normal distribution curve. Thus, probit analysis can be used to calculate the rate at which zebra mussel mortality occurs.

In probit analysis, the mortality is plotted in probit units (rather than as a percent) against time. A probit unit is a linearization of the cumulative normal distribution curve. Mussel mortality should plot as a straight line on a probit plot. A probit value of 5 corresponds to 50% mortality. Thus, the time to 50% mortality is given by:

$$T_{50} = (5-b)/m$$

where: b and m are the intercept and slope, respectively, of the linear regression lines in the plot of chlorine (Product A) and Product C runs.

TABLE A. 1

Mortality Data-
No Oxidant (Control) (Phase I)
(blank entry signifies no data)

| Time (hr) | Temp. (°C.) | 48 hr. Mortality (# dead/total #) | Observations |
|---|---|---|---|
| 0 | 20.2 | | |
| 24.75 | | 0/10 | active |
| 46.25 | 20.2 | 0/10 | active |
| 52.25 | | | active |
| 58.25 | | | active |
| 69.75 | 19.9 | 0/10 | active |
| 75.25 | | | active |
| 81.25 | | | active |
| 93.25 | 20.0 | 0/10 | active |
| 100.25 | | | active |
| 105.25 | | | active |
| 117.25 | 20.2 | 1/10 | active |
| 129.25 | | | active |
| 141.25 | 20.2 | 0/10 | all closed |
| 153.25 | | | active |
| 165.25 | 20.0 | 0/10 | active |
| 177.25 | 20.0 | 0/20 | active |

TABLE A. 2

Mortality Data-
Product A (Phase I)-Chlorine
(nominal dose = 1 mg/L; blank entry signifies no data)

| Time (hr) | Temp. (°C.) | Free Cl₂ (mg/L) | Total Cl₂ (mg/L) | 48 hr. Mortality (# dead/total #) | Observations |
|---|---|---|---|---|---|
| 0 | 20.2 | 0.78 | 1.05 | | |
| 9.5 | | 0.9 | 1.05 | | |
| 24.75 | | 0.825 | 1.05 | 0/10 | all closed |
| 35.00 | | 0.85 | 1.10 | | |
| 46.25 | 20.2 | 0.75 | 1.05 | 1/10 | all closed |
| 52.25 | | 0.75 | 1.1 | | |
| 58.25 | | 1.05 | 1.05 | | |
| 69.75 | 19.9 | 0.9 | 1.125 | 1/9 | all closed |
| 81.75 | | 1.0 | 1.2 | | all closed |
| 93.25 | 20.0 | 0.775 | 1.05 | 7/10 | >50% dead |
| 105.25 | | 0.825 | 1.075 | | closed |
| 117.25 | 20.2 | 0.825 | 1.075 | 9/11 | closed |
| 129.25 | | 0.9 | 0.975 | | >80% dead |
| 141.25 | 20.2 | 0.5 | 0.75 | 10/11 | >90% dead |
| 153.25 | | 0.6 | 0.75 | | >95% dead |
| 165.25 | 20.0 | 0.55 | 0.65 | 10/10 | >95% dead |
| 177.25 | 20.0 | 0.425 | 0.6 | 30/31 | |

TABLE A. 3

Mortality Data-
Product C (Phase I)
(nominal dose = 2.0 mg/L;
blank entry signifies no data)

| Time (hr) | Temp. (°C.) | Calc. Conc. (mg/L) | 48 hr. Mortality (# dead/total #) | Observations |
|---|---|---|---|---|
| 0 | 20.2 | 2.0 | | |
| 9.5 | | 2.2 | | |
| 24.75 | | 2.0 | 0/10 | ca. 95% closed |
| 46.25 | 20.2 | 2.2 | 010 | all closed |
| 52.25 | | 2.0 | | ca. 5% active |
| 56.25 | | 2.3 | | ca. 5% active |
| 69.75 | 19.9 | 1.8 | 0/10 | ca. 5% active |
| 75.25 | | 2.2 | | ca. 5% active |
| 81.25 | | 2.3 | | ca. 5% active |
| 93.25 | 20.0 | 1.9 | 1/11 | ca. 5% active |
| 117.25 | 20.2 | 2.1 | 2/10 | ca. 5% active |
| 129.25 | | 2.2 | | 4 or 5 active |
| 141.25 | 20.2 | 2.1 | 0/11 | 1 active |
| 153.25 | | 2.1 | | 4 or 5 siphoning |
| 165.25 | 20.2 | 1.5 | 0/8 | some siphoning |
| 177.25 | 20.0 | 2.0 | 0/30 | all closed |

TABLE A. 4

Mortality Data-
Product C (Phase I)
(nominal dose = 20 mg/L;
blank entry signifies no data)

| Time (hr) | Temp. (°C.) | Calc. Conc. (mg/L) | 48 hr. Mortality (# dead/total #) | Observations |
|---|---|---|---|---|
| 0 | 20.2 | 20 | | |
| 9.5 | | 24 | | all closed |
| 24.75 | | 24 | 1/10 | all closed |
| 46.25 | 20.2 | 22 | 0/10 | all closed |
| 52.25 | | 21 | | some dead |
| 56.25 | | 20 | | ca. 20% dead |
| 69.75 | 19.9 | 35 | 1/10 | ca. 25% dead |
| 75.25 | | 18 | | |
| 81.25 | | 23 | | ca. 25-30% dead |
| 93.25 | 20.0 | 18 | 6/9 | ca. 30-40% dead |
| 117.25 | 20.2 | 19 | 9/11 | >50% dead |
| 129.25 | | 22 | | >60% dead |
| 141.25 | 20.2 | 20 | 9/9 | >80-85% dead |
| 153.25 | | 20 | | >90% dead |
| 165.25 | 20.0 | 22 | 10/10 | 3 closed |
| 177.25 | 20.0 | 20 | 47/48 | all dead |

TABLE A. 5

Mortality Data-
Product B (Phase I)
(nominal dose = 5 mg/L;
blank entry signifies no data)

| Time (hr) | Temp. (°C.) | Calc. Conc. (mg/L) | 48 hr. Mortality (# dead/total #) | Observations |
|---|---|---|---|---|
| 0 | 20.2 | 5.0 | | |
| 9.5 | | 4.9 | | active |
| 24.75 | | 5.3 | 0/10 | active |
| 46.25 | 20.2 | 5.3 | 0/10 | active |
| 52.25 | | 5.0 | | active |
| 56.25 | | 5.2 | | active |
| 69.75 | 19.9 | 4.9 | 0/10 | active |
| 75.25 | | 5.0 | | active |
| 81.25 | | 4.8 | | active |
| 93.25 | 20.0 | 5.0 | 0/10 | active |
| 117.25 | 20.2 | 5.0 | 0/11 | active |
| 129.25 | | 5.1 | | active |
| 141.25 | 20.2 | 5.0 | 0/12 | closed |
| 153.25 | | 5.0 | | active |
| 165.25 | 20.2 | 5.1 | 0/9 | active |
| 177.25 | 20.0 | | 0/30 | active |

TABLE A. 6

Mortality Data-
Product B (Phase I)
(nominal dose = 25 mg/L;
blank entry signifies no data)

| Time (hr) | Temp. (°C.) | Calc. Conc. (mg/L) | 48 hr. Mortality (# dead/total #) | Observations |
|---|---|---|---|---|
| 0 | 20.2 | 25 | | |
| 9.5 | | 26 | | most closed |
| 24.75 | | 24 | 0/9 | half closed |
| 46.25 | 20.2 | 24 | 0/11 | active |
| 52.25 | | 25 | | active |
| 56.25 | | 25 | | active |
| 69.75 | 19.9 | 26 | 0/10 | active |
| 75.25 | | 25 | | active |
| 81.25 | | 27 | | active |
| 93.25 | 20.0 | 26 | 0/11 | active |
| 117.25 | 20.2 | 25 | 0/10 | active |
| 129.25 | | 25 | | active |
| 141.25 | 20.2 | 25 | 0/10 | closed |
| 153.25 | | 25 | | active |
| 165.25 | 20.0 | 28 | 0/9 | active |
| 177.25 | 20.0 | 25 | 3/36 | active |

TABLE A. 7

Mortality Data-
No Oxidant (Control) (Phase II)

| Time (hr) | Temp. (°C.) | 48 hr. Mortality (# dead/total #) |
|---|---|---|
| 0 | 20.5 | |
| 21.25 | 20.7 | 0/8 |
| 45.25 | 20.8 | 0/10 |
| 75.25 | 20.5 | 0/10 |
| 103.75 | 20.5 | 0/10 |
| 120.5 | 20.4 | 0/8 |
| 146.0 | 20.4 | 2/11 |
| 165.25 | 20.4 | 0/10 |
| 193.25 | 20.6 | 1/10 |
| 217.75 | 20.6 | 1/10 |

TABLE A. 8

Mortality Data-
Product A (Phase II)-Chlorine
(nominal dose = 1.0 mg/L)

| Time (hr) | Temp. (°C.) | Free $Cl_2$ (mg/L) | Total $Cl_2$ (mg/L) | 48 hr. Mortality (# dead/total #) |
|---|---|---|---|---|
| 0 | 20.5 | 0.7 | 1.0 | |
| 21.25 | 20.7 | 0.95 | 1.15 | 5/10 |
| 45.25 | 20.8 | 0.7 | 0.9 | 1/10 |
| 72.25 | 20.5 | 0.75 | 1.0 | 6/9 |
| 103.75 | 20.5 | note 1 | note 1 | |

Note 1.
Chlorine residual too high to measure (>3.5 mg/L)
average temperature: 20.6° C.

TABLE A. 9

Mortality Data-
Product C (Phase II)
(nominal dose = 5 mg/L)

| Time (hr) | Temp. (°C.) | Calc. Conc. (mg/L) | 48 hr. Mortality (# dead/total #) |
|---|---|---|---|
| 0 | 20.5 | 4.9 | |
| 21.25 | 20.7 | 4.9 | 0/10 |
| 45.25 | 20.8 | 4.9 | 1/10 |
| 72.25 | 20.5 | 4.8 | 1/10 |
| 78.75 | | 4.9 | |
| 103.75 | 20.5 | 4.4 | 1/11 |
| 120.75 | 20.4 | 3.9 | 2/13 |
| 146.0 | 20.4 | 5.3 | 3/12 |
| 165.25 | 20.4 | 4.8 | 2/9 |
| 193.25 | 20.6 | 4.9 | 3/11 |
| 217.75 | 20.6 | 5.4 | 7/10 |

TABLE A. 10

Mortality Data
Product C (Phase II)
(nominal dose = 10 mg/L)

| Time (hr) | Temp. (°C.) | Calc. Conc. (mg/L) | 48 hr. Mortality (# dead/total #) |
|---|---|---|---|
| 0 | 20.5 | 9.8 | |
| 21.25 | 20.7 | 10.8 | 0/10 |
| 45.25 | 20.8 | 11.8 | 1/10 |
| 72.25 | 20.5 | 10.0 | 5/10 |
| 78.75 | | 9.8 | |
| 103.75 | 20.5 | 9.8 | 4/10 |
| 120.5 | 20.4 | 10.0 | 6/10 |
| 146.0 | 20.4 | 11.0 | 3/10 |
| 165.25 | 20.4 | 10.0 | 9/12 |
| 193.25 | 20.6 | 10.0 | 11/11 |
| 217.75 | 20.6 | 9.0 | 10/11 |

We claim:

1. A method for controlling zebra mussels, which comprises contacting the zebra mussels, or an environment where control is desired, with a biocidally effective amount of peracetic acid.

2. The method of claim 1 wherein the environment is aqueous and the amount of peracetic acid applied to the environment is at least 0.1 ppm.

3. The method of claim 1 wherein the environment is aqueous and the amount of peracetic acid applied to the environment is at least about 5 ppm.

4. The method of claim 1 wherein the peracetic acid is applied as an aqueous solution containing at least about 1 wt % peracetic acid.

5. The method of claim 1 wherein the peracetic acid is applied as an aqueous solution of peracetic acid, acetic acid and hydrogen peroxide.

6. The method of claim 5 wherein the peracetic acid concentration in the solution is at least about 1 wt %.

7. The method of claim 5 wherein the solution additionally contains a stabilizer for the peracetic acid.

8. The method of claim 7 wherein the stabilizer is 1-hydroxyethylidene-1,1-diphosphonic acid.

9. The method of claims 1, 4 or 5 wherein the peracetic acid is applied as a solution containing at least about 5 wt % peracetic acid.

10. The method of any one of claims 1-4 wherein the environment comprises a water intake, delivery, storage, treatment or filtration system.

* * * * *